United States Patent [19]

Mendelson

[11] Patent Number: 4,774,073

[45] Date of Patent: Sep. 27, 1988

[54] METHOD OF ASSESSING HYPOTHALAMUS FUNCTION AND ANTERIOR PITUITARY HORMONE FUNCTION

[75] Inventor: Jack H. Mendelson, Rockport, Mass.

[73] Assignee: The McLean Hospital Corporation, Boston, Mass.

[21] Appl. No.: 824,661

[22] Filed: Jan. 31, 1986

[51] Int. Cl.[4] .................. A61K 31/44; A61K 49/00; G01N 31/00; G01N 33/48
[52] U.S. Cl. .................................. 424/9; 514/282; 514/800
[58] Field of Search ............... 424/9; 546/44; 514/800, 514/282

[56] References Cited

U.S. PATENT DOCUMENTS 3,332,950 7/1967 Blumberg et al. ...................... 546/45

OTHER PUBLICATIONS

Rebar, R. W., in: Yen and Jaffe (eds.), *Endocrinol: Physiol., Pathophysiol. and Clin. Mgmt.*, pp. 469–518 (1978).
Chrousos et al., *N. Engl. J. Med.*, 310: 622–626 (1984).
De Bold et al., *J. Clin. Endocrinol. Metab.*, 57: 294–298 (1983).
Orth et al., *J. Clin. Invest.*, 71: 587–595 (1983).
Besser et al., *J. Endocrinol.*, 51: 699–706 (1971).
Harsoulis et al., *Br. Med. J.*, 4: 326–329 (1973).
Lufkin, E. G. et al., *Am. J. Med.*, 75: 471–475 (1983).
Mortimer, C. H. et al., *Clin. Endocrinol.*, (Oxf) 2: 317–326 (1973).
Sheldon W. R., et al., *J. Clin. Endocrinol. Metab.*, 60: 623–630 (1985).
Briski et al., *Life Science*, 34: 2485–2493 (1984).
Veldhuis et al., *J. Clinical Invest.*, 72: 2031–2040 (1983).
Mendelson et al., *J. Pharmacol. Exp. Ther.*, 214: 503–506 (1980).
Cicero et al., *Endocrinology*, 104: 1286–1291 (1979).
Atkinson, R. L., *J. Clinical Psychiatry*, 45: 9, Part 2 at 20–24 (1984).
Snowden, E. U., *J. Clinical Endocrinology Metab.*, 59: 298–302 (1984).
Christian, M. S., *J. Clinical Psychiatry*, 45: 7–10 (1984).
Gosselin et al., *Endocrinology*, 112: 2168–2173 (1983).
Yen, S. S. C. et al, *Am. J. Obstet. Gynecol.*, 152: 485–493 (1985).
Petraglia, F. et al., *Fertility and Sterility*, 43: 534–540 (1985).
Ferin, M. et al., *Europ. J. Obstet. Gynec. Reprod. Biol.*, 18: 365–373 (1984).
Tejwani, G. A. et al., *Life Sciences*, 33: 519–522 (1983).
Ropert, J. F. et al., *J. Clin. Endocrinol. Metab.*, 52: 583–585 (1981).

*Primary Examiner*—Douglas W. Robinson
*Attorney, Agent, or Firm*—Saidman, Sterne, Kessler & Goldstein

[57] ABSTRACT

This invention is directed to a method for assessing hypothalamic function and anterior pituitary hormone function comprising administering 14-hydroxydihydronormorphinone derivatives to a patient in an amount sufficient to stimulate the secretion of anterior pituitary hormones in said patient and assessing the level of secreted hormone.

11 Claims, 4 Drawing Sheets

METHOD OF ASSESSING HYPOTHALAMUS FUNCTION AND ANTERIOR PITUITARY HORMONE FUNCTION

FIELD OF THE INVENTION

This invention relates to a method for assessing hypothalamic function by measuring the anterior pituitary hormone release function in response to the administration of 14-hydroxydihydronormorphinone derivatives.

BACKGROUND OF THE INVENTION

The anterior pituitary secretes several hormones which play a major role in metabolic functions. Among the most important of these hormones are the following: (1) thyroid-stimulating hormone (TSH) which stimulates the thyroid gland; (2) adrenocorticotropic hormone (ACTH) which stimulates the adrenal cortex to secrete cortisol; (3) growth hormone (GH) which stimulates body growth under certain circumstances; (4) follicle-stimulating hormone (FSH) which stimulates the ovaries in females and the testes in males; (5) luteinizing hormone (LH) which also stimulates the ovaries in females and the testes in males; and (6) prolactin (PRL) which stimulates secretion of milk from the breast.

The hypothalamus regulates many of the functions of the anterior pituitary by secreting a corresponding hypothalamic releasing factor which stimulates the secretion of the anterior pituitary homones. The several known hypothalamic releasing hormones include thyrotropin-releasing hormone (TRH) which stimulates the release of TSH; corticotropin-releasing hormone (CRH) which stimulates the release of ATCH; growth hormone releasing hormone (GRH); luteinizing hormone-releasing hormone or gonadotropin-releasing hormone (LHRH or GnRH) which stimulates the release of both LH and FSH; and prolactin-releasing hormone (PRH).

In evaluating the anterior pituitary function to secrete hormones, current methods involve the administration of hypothalamic releasing hormones to a patient. Assessment of anterior pituitary hormone function has been greatly facilitated by the availability of synthetic analogues of hypothalamic releasing hormones. The use of TRH and GnRH is routinely employed as specific provocative tests for assessment of anterior pituitary hormonal function. Rebar, R. W., Practical Evaluation of Hormonal Status. In: Yen, S. S. C. and Jaffe, R. B. (eds.). *Endocrinology: Physiology, Pathophysiology and Clinical Management.* Philadelphia: W. B. Saunders Co., (1978) pp. 469-518.

Recently, synthetic ovine corticotropin-releasing hormone (CRH) has been employed for assessing ACTH release from the anterior pituitary. Chrousos et al., "The Corticotropin-Releasing Factor Stimulation Test: an Aid in the Evaluation of Patients with Cushing's Syndrome," *N. Engl. J. Med.,* 310: 622-626 (1984); DeBold et al., "Effect of Synthetic Ovine Corticotropin-releasing Factor: Prolonged Duration of Action and Biphasic Response of Plasma Adrenocorticotropin and Cortisol", *J. Clin. Endocrinol. Metab.,* 57: 294-298 (1983); and Orth et al., "Effect of Synthetic Ovine Corticotropin-releasing Factor: Dose Response of Plasma Adrenocorticotropin and Cortisol, *J. Clin. Invest,* 71: 587-595 (1983).

Simultaneous sequential admission of hypothalamic releasing hormones has also been employed for determination of pituitary hormone function. Besser, G. M. et al., "Interaction Between Thyrotrophin, Coricotrophin and Growth Hormone Secretion in Man," *J. Endocrinol,* 51: 699-706 (1971); Harsoulis, P. et al., "Combined Test for Assessment of Anterior Pituitary Function," *Br. Med. J.,* 4: 326-329 (1973); Lufkin, E. G. et al., "Combined Testing of Anterior Pituitary Gland with Insulin, Thyrotropin-releasing Hormone, and Luteinizing Hormone-releasing Hormone," *Am. J. Med.,* 75: 471-475 (1983); and Mortimer, C. H. et al., "Interaction Between Secretion of the Gonadotrophins, Prolactin, Growth Hormone, Thyrotrophin and Corticosteroids in Man: the Effects of LH/FSH-RH, TRH and Hypoglycaemia Alone and in Combination," *Clin. Endocrinol.* (Oxf) 2: 317-326 (1973).

A recent study describes a rapid sequential intravenous administration procedure utilizing four hypothalamic releasing hormones which measures pituitary ACTH, FSH, LH, TSH, and PRL secretory function. Sheldon, W. R. Jr. et al., "Rapid Sequential Intravenous Administration of Four Hypothalamic Releasing Hormones as a Combined Anterior Pituitary Function Test in Normal Subjects," *J. Clin. Endocrinol. Metab.,* 60: 623-630 (1985).

These current tests assess the secretion response of the anterior pituitary to a hypothalamic releasing hormone stimulus. None of these provocative tests, however, evaluate hypothalamic function to secrete releasing hormone. Moreover, since each hypothalamic releasing hormone is relatively specific for stimulating anterior pituitary hormone release, a single hypothalamic releasing hormone administration cannot evaluate multiple hormone secretions from the anterior pituitary. Thus, the current tests require the intravenous administration of a combination of several hypothalamic releasing hormones or require the intravenous, sequential administration of a series of hypothalamic releasing hormones over a period of time.

The inventor has discovered that 14-hydroxydihydronormorphinone derivatives can be used to assess multiple anterior pituitary hormone release as a consequence of the derivatives' ability to stimulate the hypothalamus. One of these derivatives, naltrexone, an opiate antagonist, is currently utilized in conventional medical practice as a pharmacologic adjunct for the treatment of opioid dependence.

Previous studies have shown that naltrexone increases plasma LH levels in normal adults. Briski et al., "Endogenous Opiate involvement in Acute and Chronic Stress-Induced Changes in Plasma LH Concentrations in the Male Rat," *Life Science,* 34: 2485-93 (1984); Veldhuis et al., "Endogenous Opiates Modulate the Pulsatile Secretion of Biologically Active Luteinizing Hormone in Man," *J. Clinical Invest.,* 72: 2031-40 (1983); Mendelson et al., "Heroin and Naltrexone Effects on Pituitary Gonadal Hormones in Man: Interaction of Steroid Feedback Effects Tolerance and Super Sensitivity," *J. Pharmacol. Exp. Ther.,* 214: 503-506 (1980); and Cicero et al., Endogenous Opioids Participate in the Regulation of the Hypothalamus-Pituitary-Luteinizing Hormone Axis and Testosterone's Negative Feedback Control of Luteinizing Hormone," *Endocrinology,* 104: 1286-91 (1979).

The use of naltrexone to stimulate release of other anterior pituitary hormones has also been studied. Atkinson, R. L., "Endocrine and Metabolic Effects of Opiate Antagonists," *J. Clinical Psychiatry,* 45: 9, Part 2 at 20-24 (1984).

However, it was not known that the oral administration of naltrexone can be useful as a single provocative stimulus for the release of multiple anterior pituitary hormone functions, including LH, FSH, prolactin, and ACTH. The inventor has found that hypothalamic function can be assessed by measuring the anterior pituitary hormone release in response to the stimulus from the administration of a 14-hydroxydihydronormorphinone derivative to the patient. Moreover, the inventor has found that administration of the 14-hydroxydihydronormorphinone derivatives during the early follicular phase of the female menstrual cycle is most effective for assessing hypothalamic function which regulates the release of anterior pituitary hormones.

SUMMARY OF THE INVENTION

This invention is directed to a method for assessing hypothalamic function and the anterior pituitary hormone function by administering to a patient a sufficient amount of a 14-hydroxydihydronormorphinone derivative to stimulate the secretion multiple anterior pituitary hormones. The level of stimulated hormones secreted are measured and compared to a baseline hormone level in order to evaluate the hypothalamic hormone function and the anterior pituitary hormone function in the patient.

DETAILED DESCRIPTION OF THE PREFERRED EMBODIMENTS

Figure 1:
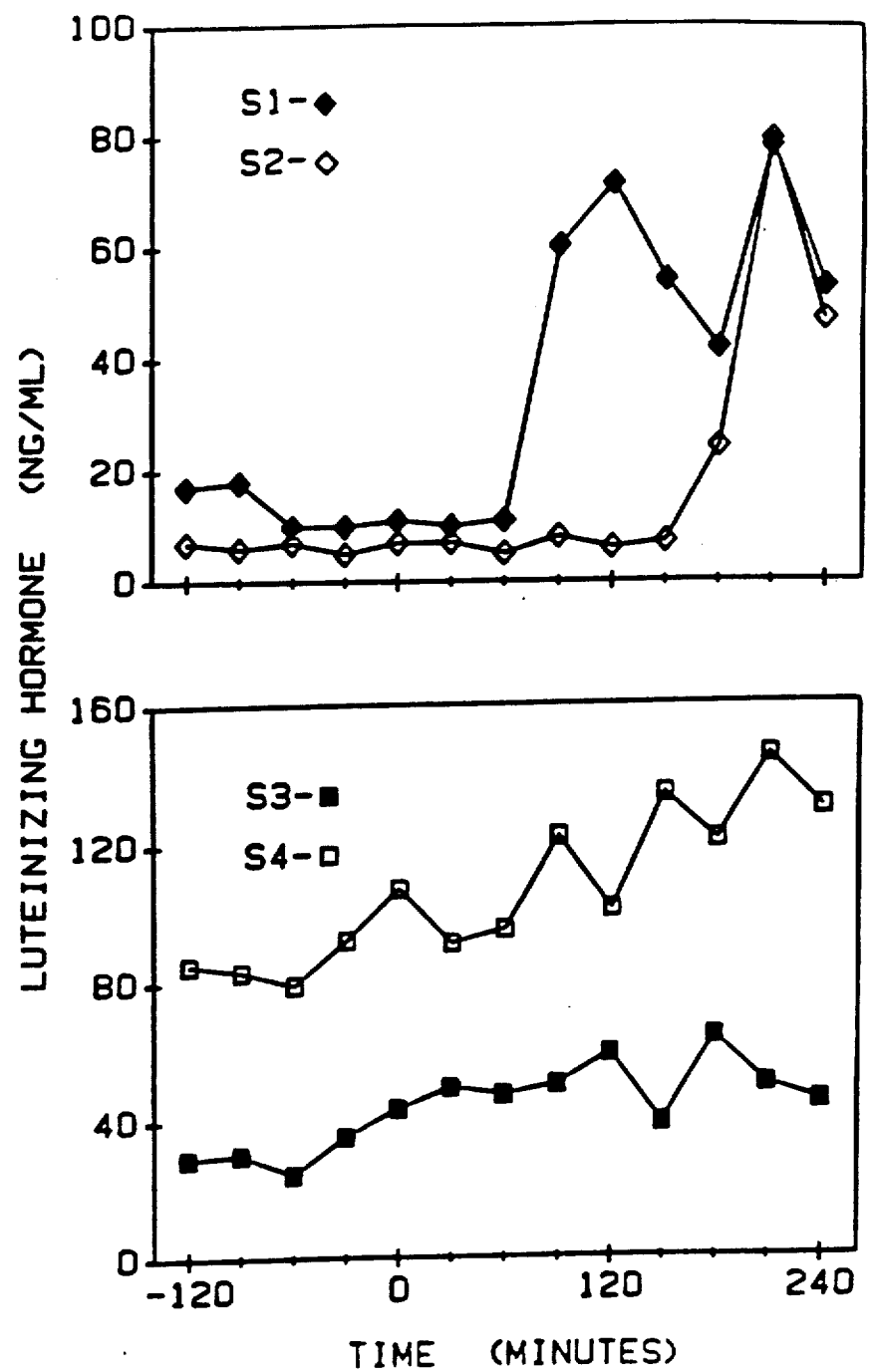
FIG. 1 shows the luteinizing hormone levels prior to and following naltrexone administration at 0 time. The top panel shows LH values for two subjects (S-1, S-2) studied during the early follicular phase of the menstrual cycle. The bottom panel shows LH values for two subjects (S-3, S-4) studied during the mid and late follicular phase of the menstrual cycle.

The present invention provides for a method of assessing hypothalamic function and the anterior pituitary hormone function by administering a 14-hydroxydihydronormorphinone derivative to a patient to stimulate the secretion of anterior pituitary hormones. According to this invention, the ability of the anterior pituitary to secrete luteinizing hormone (LH), follicle-stimulating hormone (FSH), prolactin, and adrenocorticotropic hormone (ACTH) can be assessed in a patient by the response to the administration of a 14-hydroxydihydronormorphinone derivative. Adequacy of the hypothalamic function can be inferred by the ability of the derivatives to stimulate the secretion of anterior pituitary hormones. Further, the adrenal cortex function to secrete cortisol can be measured by the anterior pituary's secretion of ACTH, which stimulates the adrenal cortex to secrete cortisol.

As used herein, 14-hydroxydihydronormorphinone derivatives are opiate antagonists comprising an N-substituted-14-hydroxydihydronormorphinone compound wherein the N-substituent is 3'-methyl-2'-butenyl, cyclopropylmethyl, or cyclobutylmethyl and pharmaceutically acceptable acid addition salts thereof. In the preferred embodiment of this invention, the 14-hydroxydihydronormorphinone derivative is N-cyclopropylmethyl-14-hydroxydihydronormorphinone hydrochloride, hereinafter referred to as naltrexone. The 14-hydroxydihydronormorphinone derivatives and the synthesis thereof are described in U.S. Pat. No. 3,332,950, incorporated herein by reference.

According to this invention, a 14-hydroxydihydronormorphinone derivative (hereinafter referred to as an HDNM derivative) is administered orally to patients to stimulate the hypothalamus and release of anterior pituitary hormones. The HDNM derivative is administered in an amount sufficient to stimulate the secretion of several anterior pituitary hormones, without causing side effects. The typical dose range of HDNM derivatives is from about 25 to 150 mg, preferably about 50 mg to about 100 mg. One skilled in the art may determine other dose ranges that are preferable depending upon the patient to be tested, for example based on age and weight considerations. These ranges may be easily determined by one of skill in the art through routine testing. The mode of administration of the derivative is preferably by oral means, although the derivative may also be administered intravenously.

In the method according to this invention, venous blood is drawn from the patient to be tested prior to HDNM derivative administration. Levels of anterior pituitary hormones, adrenal hormone (cortisol), and gonadal hormones (luteinizing hormone, follicle-stimulating hormone, and prolactin) are measured to determine a baseline hormonal level in the patient. After administration of the drug, venous blood is also drawn from the patient and the stimulated hormonal secretion is measured. The levels of stimulated hormone secretion can then be compared with the previously established baseline hormonal levels. Adequacy of hypothalamic function can be inferred from anterior pituitary hormone release following administration of the HDNM derivative according to the methods of this invention.

Although only two samples of blood, before and after HDNM derivative adminstration, are necessary to compare the basal hormonal levels with the stimulated hormonal levels, it is preferable to measure the stimulated hormonal levels at timed intervals. The HDNM derivative will have a maximum hormonal stimulatory effect for approximately 3 to 4 hours. Therefore in the preferred embodiment, the first blood sample is drawn after about 1 hour following administration of the derivative and a second blood sample is drawn about 1 hour and 45 minutes after derivative administration. It will, however, be understood in the art that other timed intervals for blood sampling after HDNM derivative administration may also be used.

The hormones secreted in response to HDNM derivative administration can also be measured in other biological fluids, including cerebrospinal fluid, urine, and saliva, although the preferable sample is venous blood.

The hormonal levels in the patient's blood samples, before and after stimulation by HDNM derivative administration, can be assayed by well known means in the art. These methods include radioimmunoassays and enzyme immunoassays, such as enzyme-linked immunosorbent assay.

In the preferred embodiment of this invention, HDNM derivatives can be used in a method of determining a female patient's reproductive function. In this method, an HDNM derivative is administered to a female patient during the early follicular phase of the menstrual cycle. The follicular phase is generally days 1 to 14 of the menstrual cycle, prior to ovulation, and beginning with the menstruation. Blood samples from the female patient, collected before and after administration of the drug, can then be evaluated for anterior pituitary hormone function by measuring the hormonal levels in both samples and comparing the stimulated hormonal levels with the baseline hormonal levels. According to the most preferred embodiment of this invention, an HDNM derivative may be administered on days 1 to 3 of menstruation, the early follicular phase, thus permitting accurate scheduling of HDNM derivative provocative tests with optimal clinical feasibility.

The use of HDNM derivatives as provocative tests for assessing the hypothalamic function and the anterior pituitary hormone function has several advantages over the now available methods. These current tests determine the anterior pituitary hormone response to hypothalamic releasing hormones, but do not directly evaluate hypothalamic function plus anterior pituitary response. According to this invention, HDNM derivative administration stimulates anterior pituitary hormone secretion as a consequence of the drug's effect on the hypothalamus, thereby assessing, at one time, both hypothalamic and anterior pituitary hormone secretion function. The HDNM derivatives act to first stimulate the hypothalamus which in turn causes a stimulation of anterior pituitary hormone release. If the hypothalamus is not functioning normally, anterior pituitary hormones will not be released following administration of HDNM derivatives. In the event that anterior pituitary hormones are not secreted in response to the HDNM derivative administration, currently existing provocative tests for stimulating anterior pituitary release of hormones using hypothalamic releasing hormone can be employed. The level of anterior pituitary hormone released in response to the hypothalamic releasing hormone administration can then be measured and compared to a baseline anterior pituitary hormone level. If anterior pituitary hormones are released, then the anterior pituitary function can be assumed to be normal and the hypothalamic function can be assumed to be abnormal. If hormones are not released, then the anterior pituitary hormone function, or the hypothalamic function, or both, can be assumed to be malfunctioning.

Currently one technique for stimulating prolactin secretion from the anterior pituitary, involves administering a synthetic thyroid-releasing hormone. Abbott Laboratories, Thypinone® (protirelin), Synthetic Thyrotropin-Releasing Hormone (TRH), In *Physicians' Desk Reference*, pp. 3002-3003 (1985). Administration of the HDNM derivative does not act in a manner similar to that of TRH, which not only stimulates prolactin release from the anterior pituitary, but also stimulates release of TSH. The inventor has found that the HDNM derivatives do not stimulate the release of TSH from the hypothalamus and also do not stimulate the release of TSH from the anterior pituitary. The HDNM derivatives apparently act directly upon the hypothalamus to stimulate anterior pituitary release of prolactin.

The following example describes the materials and methods used in carrying out the invention. The examples are not intended to limit the invention in any manner.

EXAMPLE

Four adult women, subjects one, two, three, and four, identified correspondingly as S1 to S4 at FIGS. 1 to 4, between the ages of 22 and 28 provided informed consent for participation in these studies. All women had a past history of normal menstrual cycle function. None had been pregnant and none used contraceptive medication or intrauterine devices. All had normal physical and mental status, blood chemistry, urinalysis and blood hemogram studies. No subject had any past history of alcohol or drug abuse and none were using any medications at the time of the study. Urine screens for analgesic, stimulant, depressant and other psychoactive drugs were negative.

The study was carried out during the follicular phase of the menstrual cycle. Subjects reported to the laboratory at 9 a.m. following a twelve hour fast. An indwelling catheter was placed in the antecubital vein and connected to a slow intravenous infusion of 5% dextrose and saline. Subjects were recumbent throughout the study, and were not permitted to eat solid foods, smoke or drink beverages containing caffeine. However, they could drink noncarbonated fruit juice and they were also able to read or watch television.

Following collection of four consecutive blood samples at thirty minute intervals, subjects ingested one 50 mg tablet of naltrexone hydrochloride. Blood samples were collected at consecutive thirty minute intervals for 240 minutes following naltrexone administration.

Plasma samples were aliquoted and frozen ($-70°$ C.) for subsequent analysis of LH, ACTH, prolactin and cortisol, with the results reported at FIGS. 1 to 4.

Plasma LH and prolactin levels were measured in duplicate by a double-antibody radioimmunoassay (RIA) procedure similar to that described by Midgley, A. R., Jr., "Radioimmunoassay: A Method for Human Chorionic Gonadotropin and Human Luteinizing Hormone," *Endocrinology*, 79: 10–18 (1966). Antisera and reference preparations (LER-907 for LH, hPRL-RP-1 for prolactin) were provided by the National Hormone and Pituitary Program (University of Maryland School of Medicine), supported by the National Institute of Arthritis, Diabetes and Digestive and Kidney Diseases. Iodine-125-labeled human LH and prolactin were purchased from Cambridge Medical Diagnostics (Billerica, MA). Results and expressed in terms of the LH and prolactin reference preparations. Assay sensitivities were 3.4 and 3.1 ng/ml for the LH and prolactin assays, respectively. Intra- and interassay coefficients of variation (CVs) were 5.8 and 5.4 percent for the LH assay and 6.8 and 14 percent for the prolactin assay.

Plasma ACTH concentrations were measured in duplicate using a direct double antibody radioimmunoassay kit purchased from Nichols Institute Diagnostics (San Juan Capistrano, Calif.). Assay sensitivity was 10 ph/ml. Intra- and interassay coefficients of variation were 8.1 and 22.4 percent, respectively.

Cortisol was determined in duplicate plasma samples by a direct double-antibody RIA method that did not require solvent extraction, using a kit purchased from Clinical Assays (Cambridge, MA). The assay sensitivity was less than 2 ng/dl. Intra- and interassay CVs were 3.4 and 9.4 percent.

FIG. 1 shows LH values for two subjects (1 and 2) studied during the early follicular phase of the menstrual cycle (top panel) and two subjects (3 and 4) studied during the mid and late follicular phase (bottom panel). Baseline LH levels prior to naltrexone administration for subjects 1 and 2 studied during the early follicular phase ranged between 8 to 18 ng/ml. Peak LH values were detected 210 minutes following naltrexone intake. Peak LH increments above mean baseline levels were 63 ng/ml for subject 1 and 72 ng/ml for subject 2 (500% and 1300% increments, respectively).

Subject 3 was studied during the mid follicular phase and had baseline LH values averaging 30 ng/ml. Peak LH values were detected 180 minutes following naltrexone administration. The peak increment in LH values for this subject was 33 ng/ml (95% increase above baseline values).

Subject 4 studied during the late follicular phase of the menstrual cycle had baseline LH levels averaging 90 ng/ml. Peak LH levels following naltrexone administration were detected at 210 minutes. LH levels increased by 55 ng/ml (50% increase above baseline values).

Figure 2:
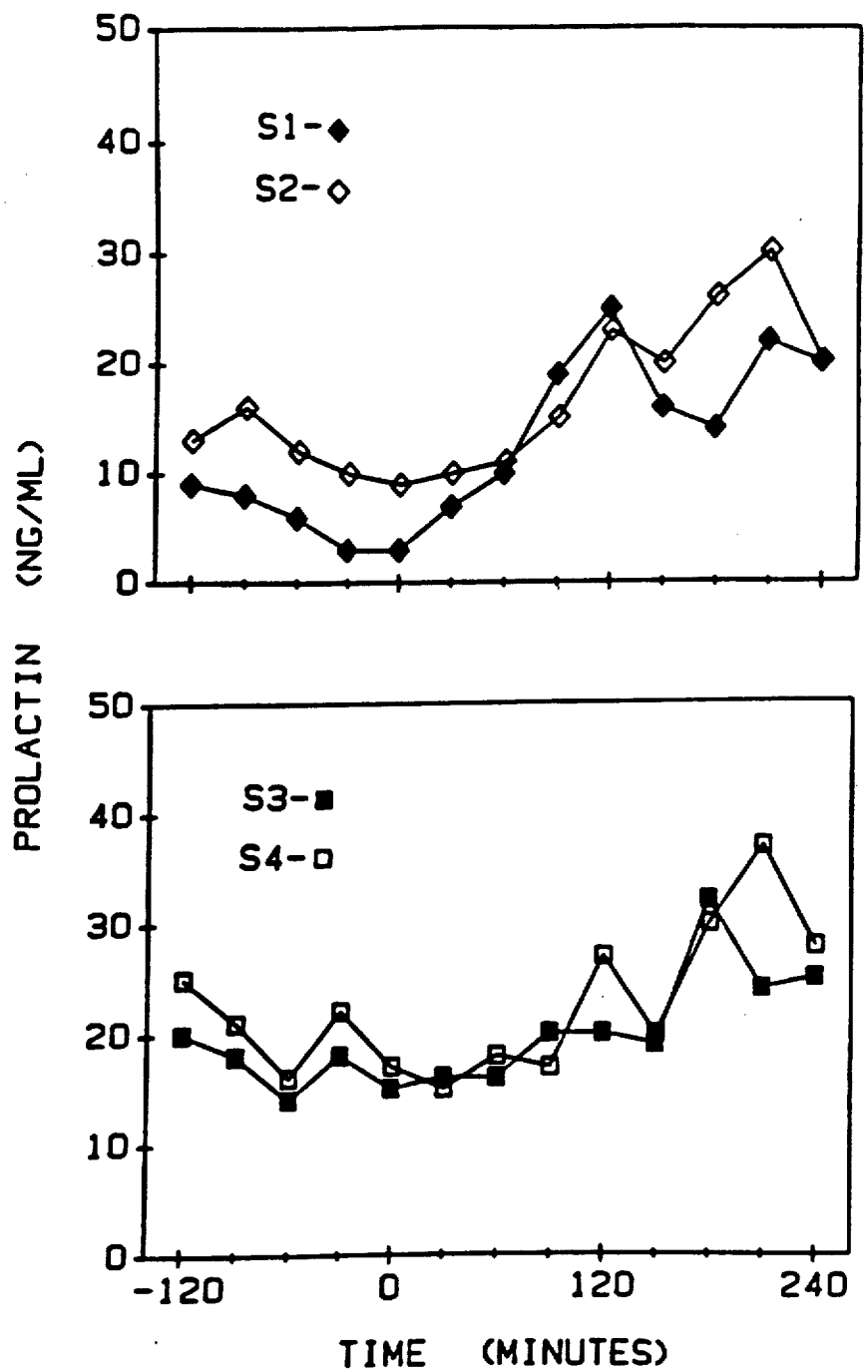
FIG. 2 shows the prolactin levels prior to and following naltrexone administration at 0 time. The top panel shows prolactin values for two subjects (S-1, S-2) studied during the early follicular phase of the menstrual cycle. The bottom panel shows prolactin values for two subjects (S-3, S-4) studied during the mid and late follicular phase of the menstrual cycle.

Prolactin levels prior to and following naltrexone administration for subjects studied during the early, mid and late follicular phase of the menstrual cycle are shown in FIG. 2. Baseline prolactin levels for the subjects studied during the early follicular phase (top panel FIG. 2) ranged between 3 and 17 ng/ml. Following naltrexone administration, peak prolactin levels were detected at 120 to 210 minutes. The peak increment in prolactin levels was 18 to 20 ng/ml or 250 to 600% above baseline values.

Subjects studied during the mid and late follicular phase of the menstrual cycle (bottom panel FIG. 2) had higher baseline prolactin levels than those women studied during the early follicular phase. Naltrexone administration induced an increase in prolactin levels 180 to 210 minutes following drug intake. Prolactin levels increased 16–18 ng/ml or approximately 100% above baseline values.

Figure 3:
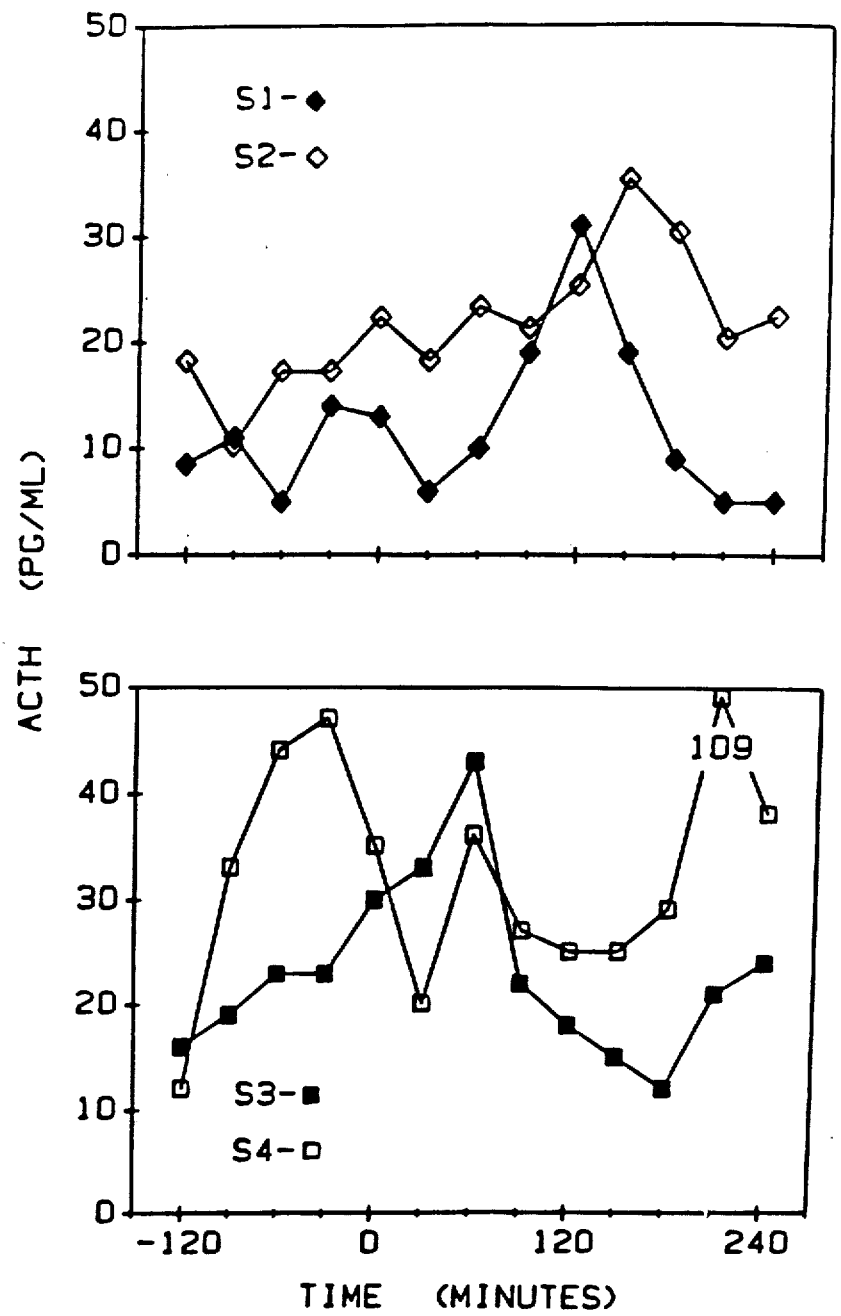
FIG. 3 shows the ACTH levels prior to and following naltrexone administration at 0 time. The top panel shows ACTH values for two subjects (S-1, S-2) studied during the early follicular phase of the menstrual cycle. The bottom panel shows ACTH values for two subjects, (S-3, S-4) studied during the mid and late follicular phase of the menstrual cycle.

FIG. 3 shows plasma ACTH levels for subjects studied during the early, mid and late follicular phases of the menstrual cycle. During the early follicular phase (top panel FIG. 3) ACTH values ranged between 5 and 22 pg/ml. Peak ACTH levels following naltrexone administration were detected 120 to 140 minutes following drug intake. Plasma ACTH levels increased by an average of 15 pg/ml or 100 to 200% over baseline values. During the mid and late follicular phase of the menstrual cycle (bottom panel FIG. 3) baseline ACTH levels ranged between 10–48 pg/ml. Subject 3 had an increase in ACTH levels which peaked at +60 minutes. Subject 4 had an ACTH increment at +210 minutes. There was considerable variation in ACTH levels for both subjects studied during the mid and late follicular phase of the menstrual cycle.

Figure 4:
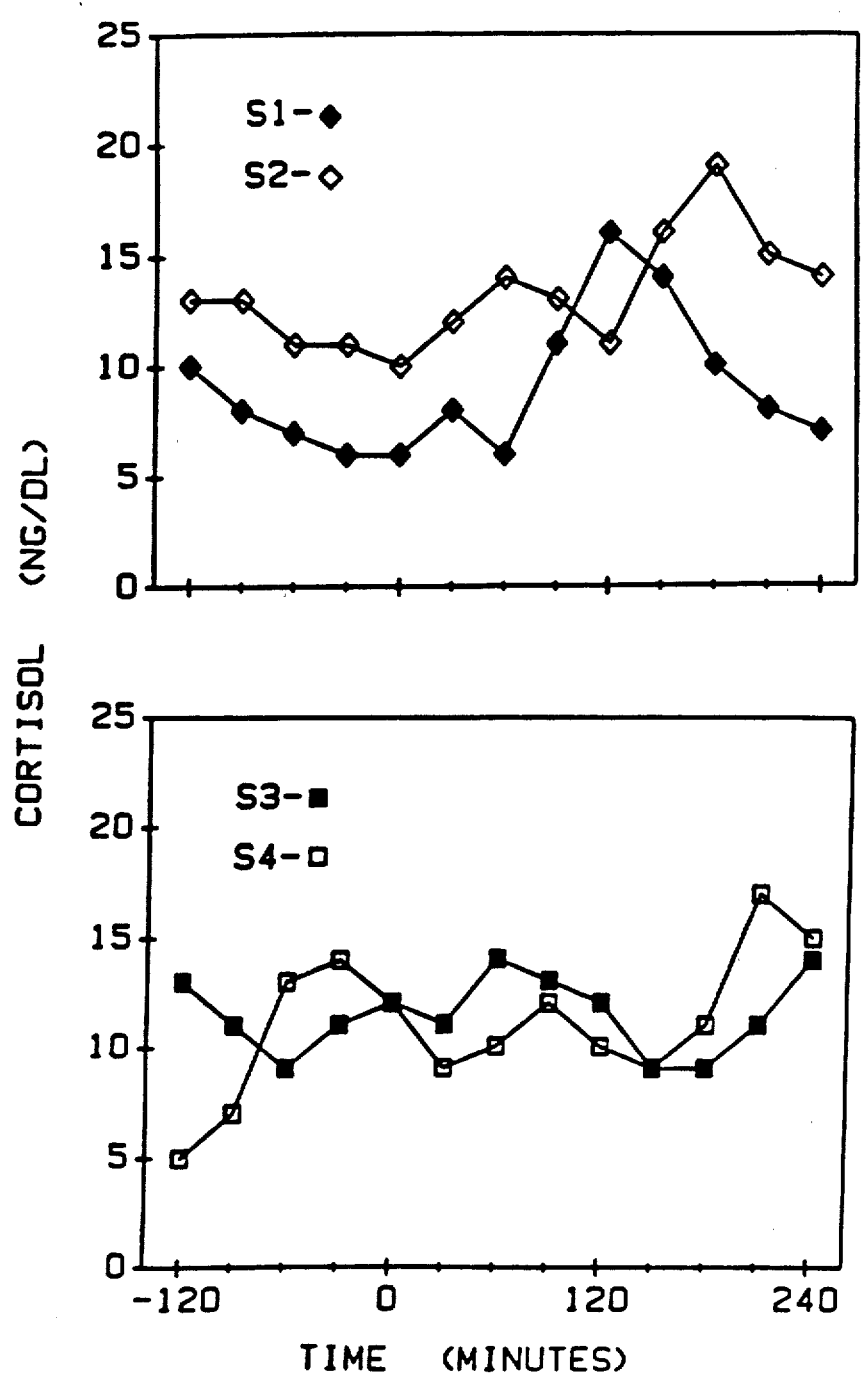
FIG. 4 shows the cortisol levels prior to and following naltrexone administration at 0 time. The top panel shows cortisol values for two subjects (S-1, S-2) studied during the early follicular phase of the menstrual cycle. The bottom panel shows cortisol values for two subjects (S-3, S-4) studied during the mid and late follicular phase of the menstrual cycle.

FIG. 4 shows plasma cortisol levels for subjects studied during the early, mid and late follicular phase of the menstrual cycle. During the early follicular phase (top panel FIG. 4) cortisol values ranged between 6 and 13 ng/dl. Peak cortisol levels following naltrexone administration were detected 120 to 180 minutes following drug intake. Plasma cortisol levels increased by an average of 8 ng/dl or 100% over baseline values. During the mid and late follicular phase of the menstrual cycle (bottom panel FIG. 4) baseline cortisol levels ranged between 9 and 13 ng/dl. Peak cortisol levels following naltrexone administration were detected 60 to 180 minutes following drug intake. Increments in plasma cortisol levels ranged between 4 to 5 ng/dl over baseline values (45% increment).

Naltrexone induced LH stimulation observed in women studied during the early follicular phase of the menstrual cycle was of greater magnitude than LH increments reported following administration of the standard dose of synthetic luteinizing hormone releasing hormone (Factrel 100 mc im). Administration of synthetic luteinizing hormone releasing hormone (Factrel 100 mc im) induces a peak increment in LH levels in women ranging between 100 and 500% above baseline values. (Ayerst Laboratories Inc. Factrel (gonadorelin hydrocholoride), Synthetic luteinizing hormone releasing hormone (LH-RH), Prescription Package Insert. 1982.)

The magnitude of the LH and prolactin response for women studied during the early follicular phase of the menstrual cycle was greater than the magnitude of LH and prolactin responses induced by the combined anterior pituitary function test described by Sheldon et al., supra.

The increase in ACTH levels following naltrexone administration to subjects studied during the early follicular phase of the menstrual cycle was concordant with the increase in plasma cortisol levels. Wide variations in baseline plasma cortisol ACTH levels were found in subjects studied during the mid and late follicular phases of the menstrual cycle.

Data obtained in this study differ from the observations of Snowden et al., "The Effect of Naloxone on Endogenous Opioid Regulation of Pituitary Gonadotropins and Prolactin During the Menstrual Cycle," *J. Clin. Endocrinol. Metab.*, 59: 298–302 (1984), based on the use of naloxone, that opioid antagonists have maximal stimulatory effects on gonadotropin and prolactin secretion during the luteal phase of the menstrual cycle.

The observations, described above, that naltrexone administration induces a large increment in plasma LH, prolactin, ACTH and cortisol levels during the early follicular phase of the menstrual cycle show that naltrexone may be employed as a provocative test for assessing hypothalamic-pituitary function.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A method of evaluating hypothalamic function and anterior pituitary hormone function in a patient comprising:
(a) orally administering to a patient a sufficient amount of an N-substituted 14-hydroxydihydronormorphinone compound, wherein the N-substituent is selected from the group consisting of 3'-methyl-2'-butenyl, cyclopropylmethyl, and cyclobutylmethyl and the pharmaceutically acceptable acid addition salts thereof, to stimulate the hypothalamic function and the anterior pituitary hormone function to secrete several anterior pituitary hormones;
(b) measuring the levels in said patient of anterior pituitary hormones secreted; and
(c) comparing said hormone levels released to baseline hormone levels for said patient.

2. The method according to claim 1 wherein the hormone is selected from the group consisting of follicle-stimulating hormone, prolactin, adrenocorticotropic hormone and a combination thereof.

3. The method according to claim 1 wherein the hormone response of the adrenal cortex in said patient is assessed by measuring the levels of cortisol secreted in response to 14-hydroxydihydronormorphinone administration and comparing the stimulated cortisol level to a baseline level.

4. A method of evaluating anterior pituitary hormone function in a patient comprising:
(a) orally administering to a patient a sufficient amount of an N-substituted 14-hydroxydihydronormorphinone compound, wherein the N-substituent is selected from the group consisting of 3'-methyl-2'-butenyl, cyclopropylmethyl, and cyclobutylmethyl and the pharmaceutically acceptable acid addition salts thereof, to stimulate the hypothalamic function and the anterior pituitary hormone function to secrete multiple anterior pituitary hormones;
(b) measuring the stimulated anterior pituitary hormonal secretion level in said patient;
(c) comparing the stimulated anterior pituitary hormonal secretion level with a baseline anterior pituitary hormonal level;
(d) assessing the anterior pituitary hormone function based on (c) and, where there is an insufficiency in at least one anterior pituitary hormonal level;
(e) administering at least one hypothalamic releasing hormone to said patient to stimulate the secretion of said at least one anterior pituitary hormone and comparing the level of said at least one anterior pituitary hormone secreted to said baseline hormonal level.

5. The method according to claims 1 or 4 wherein said 14-hydroxydihydronormorphinone compound is N-cyclopropylmethyl-14-hydroxydihydronorphinone hydrochloride.

6. The method according to claims 1 or 4 wherein said 14-hyroxydihydronormorphinone compound is administered in an amount of about 25 mg to about 150 mg.

7. The method according to claim 6 wherein said 14-hydroxydihydronormorphinone compound is administered in an amount of about 50 to about 100 mg.

8. A method for assessing hypothalamic function and anterior pituitary hormone function in a female patient, comprising the steps of:
(a) measuring the anterior pituitary hormone levels of luteinizing hormone, follicle-stimulating hormone, prolactin, and adrenocorticotropic hormone in said female patient to establish baseline hormone levels;
(b) orally administering an N-substituted 14-hydroxydihydronormorphinone compound, wherein the N-substituent is selected from the group consisting of 3'-methyl-2'-butenyl, cyclopropylmethyl, and cyclobutylmethyl and the pharmaceutically acceptable acid addition salts thereof to said female patient during the early follicular phase of said female patient's menstrual cycle in an amount sufficient to stimulate hypothalamic function and anterior pituitary hormone function to secrete said anterior pituitary hormones of step (a);
(c) measuring the stimulated anterior pituitary hormone levels; and
(d) comparing the stimulated hormone levels with baseline hormone levels for said patient.

9. The method of claim 8 wherein said 14-hydroxydihydronormorphinone compound is N-cyclopropylmethyl-14-hydroxydihydronormorphinone hydrocholoride.

10. The method of claim 8 wherein said 14-hydroxydihydronormophinone compound is administered in an amount of about 25 to about 150 mg.

11. The method of claim 10 wherein said 14-hydroxydihydronormorphinone compound is administered in an amount of about 50 mg to about 100 mg.

* * * * *